(12) United States Patent
Kim (10) Patent No.: US 7,331,242 B2
(45) Date of Patent: Feb. 19, 2008

(54) SYSTEM FOR TESTING PAVING MATERIALS

(75) Inventor: Sang-Soo Kim, Athens, OH (US)

(73) Assignee: Ohio University, Athens, OH (US)

( * ) Notice: Subject to any disclaimer, the term of this patent is extended or adjusted under 35 U.S.C. 154(b) by 132 days.

(21) Appl. No.: 11/088,438

(22) Filed: Mar. 24, 2005

(65) Prior Publication Data

US 2005/0178209 A1    Aug. 18, 2005

Related U.S. Application Data (63) Continuation-in-part of application No. 10/524,907, filed on Feb. 17, 2005, now Pat. No. 7,252,012.

(60) Provisional application No. 60/555,943, filed on Mar. 24, 2004.

(51) Int. Cl.
*G01L 1/00* (2006.01)
(52) U.S. Cl. .......................................... 73/766; 73/803
(58) Field of Classification Search ................. 73/766, 73/803, 818–824
See application file for complete search history.

(56) References Cited

U.S. PATENT DOCUMENTS

| | | | |
|---|---|---|---|
| 4,127,840 A | 11/1978 | House | |
| 4,425,808 A | 1/1984 | Rand | |
| 4,498,231 A | 2/1985 | Rand | |
| 4,507,975 A | 4/1985 | Bittner et al. | |
| 4,763,531 A | 8/1988 | Dietrich et al. | |
| 4,821,584 A | 4/1989 | Lembke | |
| 5,036,709 A | 8/1991 | McRae | |
| 5,248,200 A | 9/1993 | Walsh | |
| 5,394,753 A | 3/1995 | Moriyoshi | |

(Continued)

FOREIGN PATENT DOCUMENTS

JP        05087716        4/1993

(Continued)

OTHER PUBLICATIONS

Bahia, et al. Characterization of Modified Asphalt Binders in Superpave Mix Design, NCHRP Report 459, Transportation Research Board, National Research Council, Washington, DC (2001).

(Continued)

*Primary Examiner*—Andre J. Allen
*Assistant Examiner*—Jermaine Jenkins
(74) *Attorney, Agent, or Firm*—Calfee, Halter & Griswold LLP (57) ABSTRACT

A system for measuring the critical temperatures for thermal cracking of asphalt binders. The exemplary embodiment comprises a metal ring, at least one strain gauge attached to the inner surface of the ring, an environmental chamber, and a data acquisition system. A thermocouple may also be attached to the inside of the ring to monitor the ring temperature. A mold is provided for creating a circular asphalt binder test specimen. When properly cast, the specimen encircles the metal ring. The specimen and ring are placed within the environmental chamber for analysis as the temperature within the chamber is lowered. Thermal stress induced by temperature reduction within the asphalt binder test specimen is monitored by the strain gauge(s) and the cracking temperature is directly determined from the strain reading.

18 Claims, 6 Drawing Sheets

U.S. PATENT DOCUMENTS

| | | | |
|---|---|---|---|
| 5,659,140 | A | 8/1997 | Jakob et al. |
| 5,712,431 | A | 1/1998 | Vilendrer |
| 5,844,053 | A | 12/1998 | Nishida |
| 5,904,760 | A | 5/1999 | Hayner |
| 5,905,212 | A | 5/1999 | Moses et al. |
| 6,408,683 | B2 | 6/2002 | Bahia et al. |
| 6,792,815 | B2 | 9/2004 | McDearmon et al. |
| 2004/0019177 | A1 | 1/2004 | Brugel et al. |

FOREIGN PATENT DOCUMENTS

| | | |
|---|---|---|
| JP | 06174614 | 6/1994 |

OTHER PUBLICATIONS

Bouldin, et al. Predicting Thermal Cracking of Pavements From Binder Properties: Theoretical Basis and Field Validation, Journal of Association of Asphalt Paving Technologists, (2000), vol. 69, pp. 455-496.

Hibbeler, R.C. Mechanics of Materials, Third Edition, Prentice-Hall, Upper Saddle River, New Jersey (1997), pp. 136-138, 143-144, 152.

Hills, J.F. Predicting the Fracture of Asphalt Mixes by Thermal Stresses, Institute of Petroleum, (1974), vol. 74-014.

Hossain, et al. Quantifying Early-Age Stress Development and Cracking in Low Water-to-Cement Concrete Using the Restrained-Ring Test with Acoustic Emission, Presented at 82d Transportation Research Board Meeting (TRB 2003 Annual Meeting CD/ROM).

Kennedy, et al. Superior Performing Asphalt Pavements (Superpave): The Product of the SHRP Asphalt Research Program, SHRP-A-410, (1994), Strategic Highway Research Program, National Research Council, Washington, DC.

Masad, et al. Modeling and Experimental Measurements of Strain Distribution in Asphalt Mixes, Journal of Transportation Engineering, (2001), vol. 127, No. 6, pp. 477-485.

Roy, et al. Low-Temperature Binder Specification Development, Transportation Research Record, (2001), 1766, pp. 7-14.

Shah, et al. A Method to Predict Shrinkage Cracking of Concrete, ACI Materials Journal, (Jul.-Aug. 1998), pp. 339-346.

Van Der Poel, C. A General System Describing the Visco-Elastic Properties of Bitumens and its Relation to Routine Test Data, Journal of Applied Chemistry, (1954), vol. 4, pp. 221-236.

Notification of Transmittal of the International Search Report or the Declaration, dated Mar. 3, 2004 for PCT/US03/26459.

SYSTEM FOR TESTING PAVING MATERIALS

CROSS-REFERENCE TO RELATED APPLICATIONS

This application is a continuation-in-part of U.S. patent application Ser. No. 10/524,907, filed on Feb. 17, 2005 now U.S. Pat. No. 7,252,012 and entitled "Device and Method for Testing Paving Materials," which claimed priority to PCT application PCT/US03/26459, filed on Aug. 22, 2003 and entitled "Device and Method for Testing Paving Materials," which claimed priority to U.S. Provisional Patent Application Ser. No. 60/405,532, filed on Aug. 23, 2002 and entitled "Device and Method for Testing Paving Materials, the disclosures of which are incorporated as if fully rewritten herein. This patent application also claims the benefit of U.S. Provisional Patent Application Ser. No. 60/555,943 filed on Mar. 24, 2004 and entitled "Device and Method for Testing Paving Materials," the disclosure of which is incorporated as if fully rewritten herein.

TECHNICAL FIELD OF THE INVENTION

The present invention relates generally to devices for testing the characteristics of construction materials such as asphalt and concrete and specifically to a circular metal device and associated method for characterizing the failure modes of asphalt binders.

BACKGROUND OF THE INVENTION

Asphalt is a general term that refers to the various bituminous substances that are used extensively for paving and road making. Asphalt binders function as adhesion promoters for asphalt mixtures or aggregates and are typically comprised of naturally occurring hydrocarbons or petroleum distillate residue with or without polymer or chemical modifiers. In the paving industry, the term "aggregate" is used for a mass of crushed or uncrushed stone, gravel, sand, etc., predominantly composed of individual particles, but in some cases including clays and silts. The performance characteristics of asphalt binders are of particular importance in roadway construction. Understanding the limitations of the materials used for roadway construction permits the design and construction of roadways that are more stable, durable, and that offer greater safety to the user of the roadway.

Low temperature thermal shrinkage cracking is one of four major failure modes in asphalt pavement, together with rutting, fatigue cracking, and moisture damage. Thermal shrinkage cracking in asphalt pavement occurs when the thermal tensile stress within the asphalt pavement that results from temperature drop exceeds the strength at that temperature. Thermal cracks typically appear as transverse cracks (pavement cracks perpendicular to the direction of traffic) at regular intervals in the field pavements.

Historically, thermal cracks occurring at low temperatures have been controlled by limiting the asphalt binder stiffness. Assuming similar asphalt binder tensile strengths and coefficients of thermal expansion/contraction, the binders with a higher stiffness will crack at a higher temperature than softer binders. Because an accurate and easy to use measuring instrument was not available, the cracking temperature or the limiting low temperature stiffness of asphalt binder had been extrapolated from consistencies measured at higher temperatures, such as penetrations at 5 and 25° C., viscosity at 25° C., or ring-and-ball softening point (50-60° C.). Hill, J. F., Inst. Petroleum, vol. 74-014 (1974) and Van der Poel, C., Journal of Applied Chemistry, vol. 4, 221-236 (1954).

In the United States, the Association of American State Highway and Transportation Officials (AASHTO) has published and implemented a series of performance graded ("PG") binder specifications. These specifications were the result of the Strategic Highway Research Program (SHRP) which was conducted from 1987-1994. The SHRP/AASHTO system for specifying asphalt binders is unique in that it is a performance-based series of specifications. Various binders are categorized on the basis of the climate and attendant pavement temperatures at which the binder is expected to operate.

Under this system, physical property requirements remain the same, but the temperature at which the binder must attain the properties, changes. For example, a binder graded as PG 64-22 possesses adequate physical properties up to 64° C., which would be the high pavement temperature corresponding to the climate in which the binder is expected to operate. Similarly, the PG 64-22 binder possesses adequate physical properties down to at least minus 22° C. Thus, as illustrated by this example, the thermal characteristics of an asphalt binder are central to this grading system.

As will be appreciated by those skilled in the art, low-end temperatures of PG grading are typically determined by utilizing one or more of several known systems including the Bending Beam Rheometer (BBR) and/or the Direct Tension Tester (DTT). While effective at generating useful data, these systems are complex, require the performance of numerous calculations, require the testing of many specimens, do not directly measure the temperature at which the specimen fails, and are often very time consuming and expensive to perform. Thus, there is a need for a low-cost device and method that quickly and accurately characterizes the critical thermal characteristics of asphalt binder and aggregate specimens.

SUMMARY OF THE INVENTION

These and other deficiencies of the prior art are overcome by the present invention, the exemplary embodiment of which provides a system for analyzing construction materials such as asphalt binder. The exemplary embodiment of this system measures the critical temperatures for thermal cracking of asphalt binders and includes: a test sample; a mold for containing a test specimen, wherein the test specimen comprises the test sample and wherein the shape of the test specimen is determined by the mold; a device for characterizing the test specimen, wherein the device further comprises a metal ring in communication with the test specimen and at least one sensor in communication with the ring; and a means for changing the temperature of the test specimen at a controlled rate; and a data processing system in communication with the sensor for processing data gathered from the sensor.

Another embodiment of this invention provides a device for analyzing a specimen of asphalt binder. This device includes a silicon or metal mold for casting a test specimen; a device for characterizing the test specimen, wherein the device further comprises: a metal ring; at least one sensor (e.g., a strain gauge) in communication with the ring; and a data processing system (e.g. a computer) in communication with the sensor for processing data gathered from the sensor. Development of thermal stress (induced by temperature reduction) within the asphalt binder test specimen is monitored by the strain gauge and the cracking temperature is directly determinable from the strain reading.

Another embodiment of this invention provides a method for analyzing materials such as asphalt binder. An exemplary embodiment of this method includes the steps of heating a test sample; placing a testing device within a mold, wherein the mold further comprises a well, and wherein the device is substantially centered within the well and defines an annular space therewith, and wherein the device further comprises: a metal ring and at least one sensor in communication with the ring; creating a test specimen in the well by pouring the heated test sample into the annular space and allowing the test specimen to cool; attaching the at least one sensor to a data processing system; changing the temperature of the test specimen and the testing device at a controlled rate; and processing the data received from the sensor as the temperatures of the test specimen and the testing device change over time.

Further advantages of the present invention will become apparent to those of ordinary skill in the art upon reading and understanding the following detailed description of the preferred embodiments.

BRIEF DESCRIPTION OF THE DRAWINGS

The accompanying drawings, which are incorporated into and form a part of the specification, schematically illustrate one or more exemplary embodiments of the invention and, together with the general description given above and detailed description of the preferred embodiments given below, serve to explain the principles of the invention.

DETAILED DESCRIPTION OF THE INVENTION

The present invention provides a device and method for inducing a thermal crack in a test specimen in a manner that simulates the conditions experienced by asphalt binder found in the field. This device measures the cracking temperature and the thermal stress experienced by the test specimen under experimental conditions. The present invention measures the critical temperatures for thermal cracking of asphalt binders by using the dissimilar coefficients of thermal expansion for asphalt binders and common metals, such as aluminum. Aluminum has a modulus of elasticity that is about ⅓ of steel and consequently shows three times larger strain response, i.e., better resolution, for the same stress development.

In the most generic sense, the exemplary embodiment of the present invention comprises a metal ring, a strain gauge attached to the inner surface of the ring, an environmental chamber, one or more signal amplifiers, and data acquisition system. A thermocouple may also be attached to the inside of the tube to closely monitor the ring temperature. An asphalt binder test specimen is molded onto the outside of the aluminum ring prior to analysis of the specimen. Development of thermal stress, due to temperature reduction, within an asphalt binder test specimen is monitored by the strain gauge and the cracking temperature is directly determinable from the strain reading. It should be noted that thermal cracking of asphalt pavement is significantly influenced not only by binder properties but also mix properties such as binder contents, gradation, mastic composition, etc. Furthermore, strain distribution within asphalt binders under compressive and thermal loading is not uniform. Despite these variables, the method of the present invention assumes uniform stress-strain conditions for typical hot mix asphalt and is intended to grade asphalt binders according to their performance to minimize premature thermal cracking.

Asphalt binders have much larger coefficients of thermal expansion/contraction ($170$-$200 \times 10^{-6}/°$ C.) than aluminum ($24 \times 10^{-6}/°$ C.). As the environmental temperature drops, the differential thermal contraction (i.e., more rapid contraction of asphalt binder than that of aluminum) creates thermal stress and eventually thermal cracks appear in the specimen. Strain in the aluminum ring caused by this thermal stress is measured by the electrical strain gauge and used to calculate stress in the asphalt binder. When the test specimen cracks, the accumulated thermal stress is relieved and is shown as a sudden drop in the strain reading. The cracking temperature of the asphalt binder is directly determined as the temperature where the sudden drop of measured strain occurs. By varying the geometry of asphalt binder specimens, the field strain and strain rate conditions can be closely simulated by the experimental method of this invention. Adjusting the wall thickness of the aluminum ring can also closely simulate the effects of aggregate properties on the critical temperature.

The present invention is suitable for characterizing materials such as neat or modified asphalt binders and other similar viscoelastic materials including certain polymers. Using the device and methods of this invention, asphalt and other thermoplastic polymers can be heated, formed into a ring-shaped specimen, and tested for certain desired characteristics.

Figure 1:
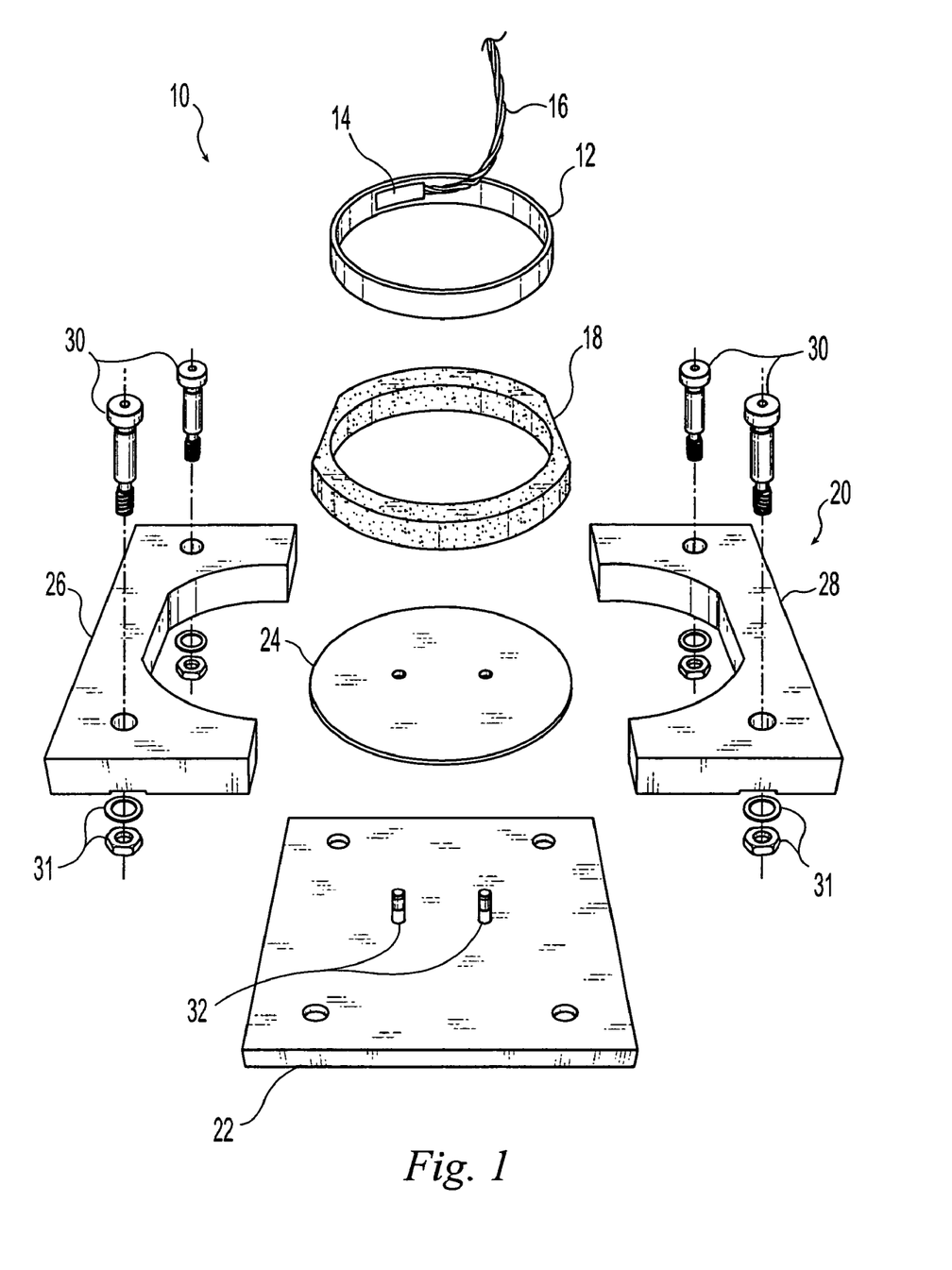
FIG. 1 is an exploded, perspective view of the mold and ring portion of the system of the present invention.
Figure 2:
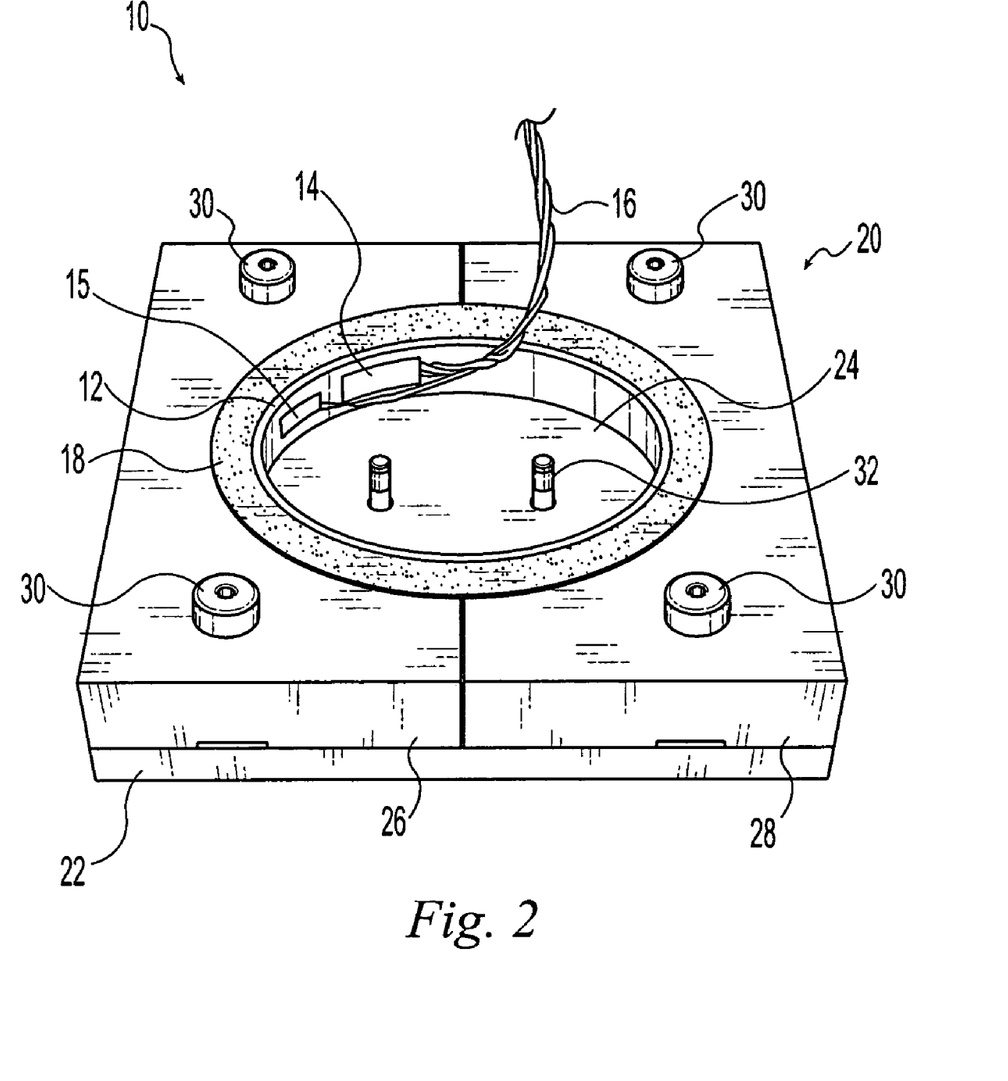
FIG. 2 is a perspective view of the mold and ring portion of the system of the present invention.
Figure 3:
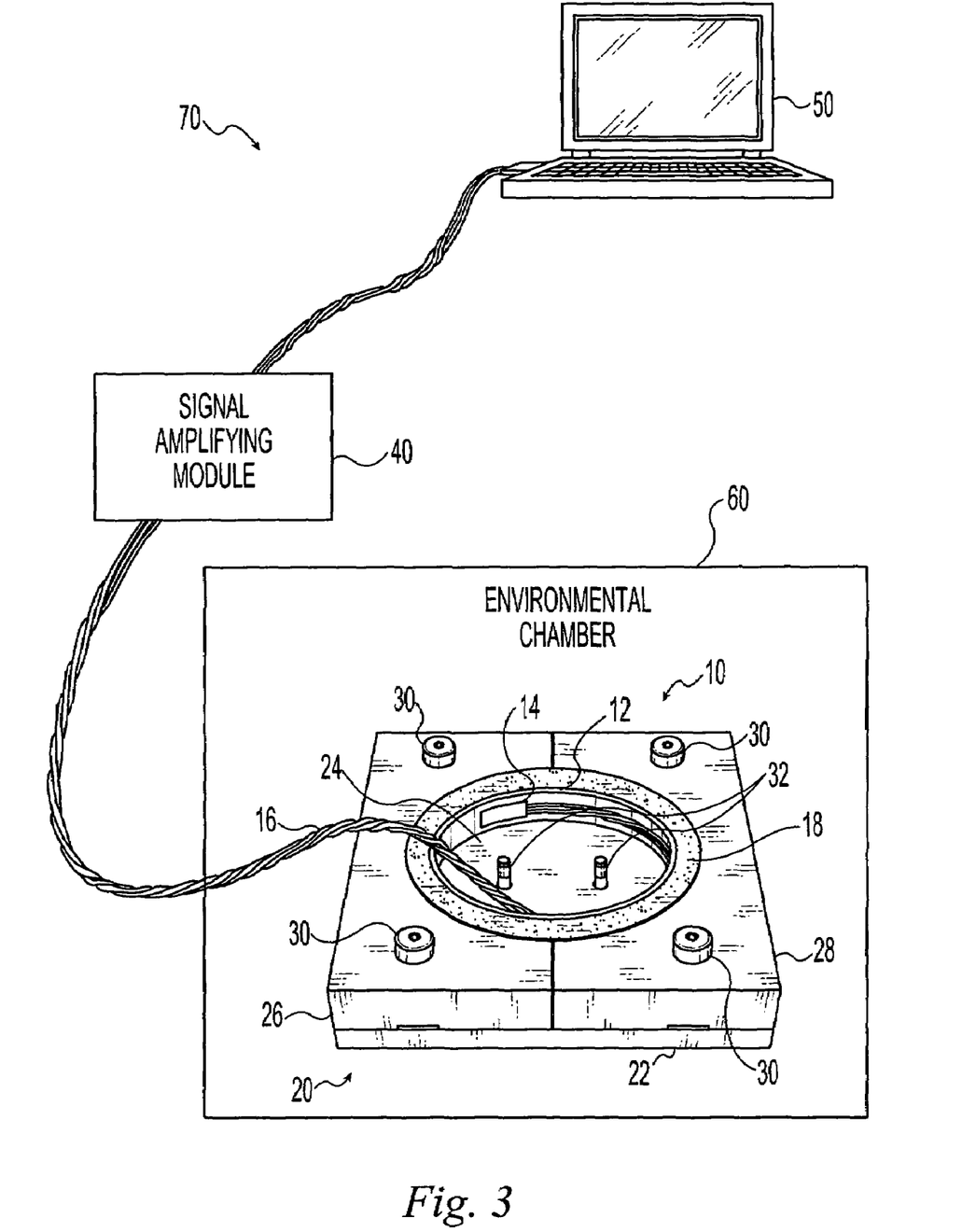
FIG. 3 is a perspective view of the system of the present invention illustrating the system components of an exemplary embodiment.

As shown in FIG. 1-2, materials testing device 10 includes a ring 12, a strain gauge 14, and lead wires 16. Materials testing device 10 also comprises a mold 20 for creating the test specimen 18. As best shown in FIG. 3, system 70 also includes a signal amplifier 40 for amplifying the electrical signal generated by the strain gauge, a data acquisition system or processor 50 for gathering data and performing the desired calculations, and an environmental chamber 60 for controlling the temperature to which the test sample is subjected. Each of the system components is described in greater detail below.

In an exemplary embodiment of the present invention, ring 12 is constructed from aluminum tubing having an outer diameter of about 50.8 mm, a height of about 12.7 mm, and a thickness of about 1.65 mm. Test rings having a variety of wall thickness can be utilized with the present invention to effectively simulate and characterize the thermal cracking phenomenon experienced by pavement materials in the field. Alternate embodiments of ring 12 utilize aluminum rings having wall thicknesses of approximately 0.005, 0.035, and 0.049 inches (0.013, 0.089, and 0.125 cm). Although aluminum is used in the exemplary embodiment, other types of metal, metal alloys, or other materials that have strain characteristics that can be accurately measured, i.e., about 100 microstrains, are compatible with the present invention. The suitability of various metals for use with the present invention can be determined empirically by placing an asphalt specimen outside of a metal test ring (0.5 inch×0.25 inch cross-section area) and measuring the strain experienced by the ring when the specimen reaches the limits of its tensile strength at a low temperature.

Mechanical strain experienced by ring 12 while specimen 36 contracts is detected by one or more electrical strain gauges 14 that are attached to the interior surface of ring 12. Data gathered from the strain gauge is transmitted through lead wires 16 to processor 50. In general, strain gauges can be described as mechanical transducers which are used to measure body deformation, or strain, applied to the area of a rigid body. Electrical resistance strain gauges are strain sensitive when bonded to the surface of a test material. When the strain gauge is stretched or compressed, its electrical resistance changes in direct proportion to the strain. By measuring the change in electrical resistance experienced by the strain gauge, the strain experienced by a test material in may be quantified.

In an exemplary embodiment, a precision strain gauge available from the Micro-Measurements Division of Vishay Measurements Group (CEA-13-500UW-120) is used to obtained experimental data useful for characterizing a test specimen. This type of gauge is a general purpose Constantan strain gauge commonly used in experimental stress analysis. Each commercially purchased gauge of this type is supplied with a fully encapsulated grid and exposed copper-coated integral solder tabs and has the following properties: (i) a temperature range of −75° C. to 205° C.; (ii) a gauge length of 0.500 inch; (iii) self-temperature compensated; (iv) strain limit: approximately 5% of the gauge length; (v) fatigue life: $10^5$ cycles at ±1800 μm/m; and (vi) a resistance of 120 Ohms. In alternate embodiments, a smaller size strain gauge (⅛ inch gauge length, EA-13-125BZ-350 also available from Micro-Measurements) with specifications similar to the gauge described above is utilized. Smaller size strain gauges facilitate the placement of centering plate 24 during preparation of the test specimen. The mechanical strain experienced by ring may also be detected with other forms of measuring devices, such as Linear Variable Differential Transduces (LVDTs) placed inside of the ring 12.

As shown in FIG. 2, one or more thermocouples 15 may be attached to the inner surface area of ring 12 or near the test specimen. These thermocouples detect and measure temperature changes experienced by the ring and the specimen 18. In an exemplary embodiment, a Type T thermocouple (SA-T-72-SC) from Omega Engineering Inc. having the following properties is used: (i) response time: less than 0.3 seconds; (ii) temperature range: minus 60° C. to 175° C.; (iii) high temperature polymer lamination and fiberglass reinforced polymer layers; (iv) length: 72 inches; (v) alloy combination: positive (+) lead: copper and negative (−) lead: Constantan copper-nickel; (vi) and an error of (above 0° C.): greater of 1.0° C. or 0.75%.

As shown in the Figures, a mold 20 is a basic component of the present invention. Mold 20 may be manufactured from a variety of metals including aluminum and steel. Mold 20 is used to create substantially circular test specimens for use with materials testing device 10. In an exemplary embodiment, mold 20 further includes base plate 22, centering plate 24, and first and second specimen supports 26 and 28. Centering plate 24 is mounted on the top surface of base plate 22 and held in the proper position by dowel pins 32. The specimen supports are also mounted on the top surface of base plate 22 and are secured to the base plate by shoulder bolts 30. Shoulder bolts 30 are secured to the base plate by washer/nut combination 31. In an exemplary embodiment, base plate 22 is about 10.2 cm in length and about 10.2 cm in width. Centering plate 24 is about 47.50 mm in diameter and about 3.18 mm thick. The two specimen supports are about 12.7 mm thick.

Ring 12 is placed around centering plate 20 prior to casting the test specimen in the mold. An exemplary embodiment of the assembled mold creates a ring-shaped test specimen, which is about 2.5 inches (6.35 cm) in diameter. The walls of the ring-shaped test specimen are about 0.25 inches thick. In an alternate embodiment of the present invention, the inner walls of specimen supports 26 and 28 are not a smooth arc-shape, but include a straight edge portion (see FIG. 1). The length of straight edge portion may be varied by the user of this invention based on the type and composition of the asphalt pavement being tested. Presumably, tests specimens molded to have straight edges more accurately replicated the thermal contraction experienced by materials in use in the field.

In the exemplary embodiment of the present invention, strain detected by the strain gauge(s) and temperature changes detected by the thermocouple(s) are amplified by signal amplifiers, typically referred to as "modules", prior to being routed to the data processing unit. Modules suitable for the testing and characterization described herein include the AD-1 808FB-1 Analog Input Module and a handheld digital thermometer (similar to HH81A thermometer from Omega Engineering Inc.).

The AD-1 808FB-1 Analog Input Module, manufactured by Optim Electronics Corporation of Germantown, Md., interacts with the strain gauges. Each 808FB-1 has eight independent channels for measuring one-quarter, one-half, and full bridge strain gauges. This module operates as two groups of four channels. The groups are divided into channels 0-3 and 4-7, with each channel receiving the same gain, excitation and voltage. Each parameter is jumper selectable. Jumper settings provides for addressing 2, 5, or 10-volt excitation voltage sources, calibration voltage, gain and filter frequency for each bank of channels along with other parameters. Each analog input module requires a Screw Terminal Block (STB). STBs provides for an easy connection between the sensors and the analog input cards. The STB 808FB-1 has two major functions. First, it allows for an interface between the lead wire of the one-quarter, one-half and full bridge strain gauges. Second, it provides for bridge completion of the one-quarter and one-half bridge strain gauges. Interfacing is provided for eight channels. Five screw terminals are allocated for each channel. Each channel requires that jumpers be set for one-quarter, one-half or full bridge application. In the present invention, a handheld digital thermometer (similar to HH81A thermometer from Omega Engineering Inc.) was used to read the signal (temperature) manually from the thermocouple placed with the test specimen.

In an alternate embodiment, a compact data acquisition system from the National instruments (NI) is utilized to collect strain and temperature data during the test. The alternate data acquisition system consists of the NI LabVIEW, NI PCI-6036E multifunction I/O, NI SCC-TC02 thermocouple input modules, and NI SCC-SG01 strain gauge input modules. LabVIEW is a graphical development environment with built-in functionality for data acquisition, instrument control, measurement analysis, and data presentation and provides the flexibility of a programming language without the complexity of traditional development environments.

The NI PCI-6036E has sixteen 16-bit analog inputs and two 16-bit analog outputs. In addition, it has 8 digital I/O lines and two 24-bit, 20 MHz counter/timers. Depending on the hard drive, the PCI-6036E can stream-to-disk at rates up to 200 kS/s. The NI SCC-SG01 consists of four models of 2-channel strain gauge input modules, each designed for a particular strain gauge configuration: 120 ohm quarter-bridge, 350 ohm quarter-bridge, half-bridge, and full-bridge. Each channel of these modules includes an instrumentation amplifier, a 1.6 kHz lowpass filter, and a potentiometer for bridge offset nulling. Each SCC-SG01 module also includes a single 2.5 V excitation source. The NI SCC-TC02 is a single-channel module for conditioning a variety of thermocouple types, including J, K, T, B, E, N, R, and S, and millivolt inputs with a range of ±100 mV. The SCC-TC modules include a 2 Hz lowpass noise filter, instrumentation amplifier with a gain of 100, and buffered outputs. The input circuitry of the SCC-TC modules also includes high-impedance bias resistors for open-thermocouple detection as well as handling both floating and ground-referenced thermocouples. The SCC-TC modules include an onboard thermistor for cold-junction compensation.

In the exemplary embodiment of the present invention, a Megadac 5414AC data acquisition system, manufactured by Optim Electronics Corporation of Germantown, Md., was used to monitor and record strain sensor response presented in the exemplary test data. The Megadac 5414AC is a 16-bit system with 256 megabytes of acquisition and storage memory. Data, i.e., time and strain gauge signals in microstrain, was collected at one sample per second per sensor and filtered at 100 Hz. A portable computer with windows operating system was used to operate the Megadac. The self-contained Megadac data acquisition system was controlled through an interactive IEEEE-488 communications bus. Optim provided its own Test Control Software (TCS) for the data acquisition system. TCS is windows based software used to communicate, setup, and acquire data from the Megadac. Using TCS, real time display of test time and the strains were presented in tabular and graphic forms during the test. Megadac is also capable of storing sensor identification and data confirmation information as well as provide an output format for the final results. Settings for the strain gauges used in this invention were 5 volts excitation and 2.115 gauge factor.

Data collected by Megadac were exported as text format and read into Micrsoft Excel spread sheet. Time and temperature data collected manually were combined with the Megadac data in Excel for determination of the cracking temperature and the tensile strength of the specimen by plotting temperature versus strain.

An alternate embodiment of this system utilizes the National Instruments, LabVIEW and NI PCI-6036E multifunction I/O to collect test time, strains, and temperature data simultaneously. NI LabVIEW is a graphical development environment with built-in functionality for data acquisition, instrument control, measurement analysis, and data presentation performing similar to the Megadac system. LabVIEW provides the flexibility of a programming language without the complexity of traditional development environments. The NI PCI-6036E has sixteen 16-bit analog inputs and two 16-bit analog outputs. In addition, it has 8 digital I/O lines and two 24-bit, 20 MHz counter/timers. Depending on hard drive, the PCI-6036E can stream-to-disk at rates up to 200 kS/s.

During the analysis of a test specimen, materials testing device 10 is placed in an environmental chamber 60 that simulates the low temperature extremes experienced by asphalt binders and other materials in the field. Environmental chambers suitable for use with the present invention include any programmable refrigeration device that permits the user to lower the internal temperature of the chamber at a constant rate to below minus 50° C. using air or liquid fluid as cooling medium. Suitable liquid mediums in a bath for temperature control include ethanol, methanol, and glycol-methanol mixtures.

Having generally described this embodiment, a further understanding can be obtained by reference to the example detailed below, which is provided for purposes of illustration only and are not intended to be all inclusive or limiting unless otherwise specified.

EXAMPLE I

Preparation of Mold and Test Specimen

A test specimen of asphalt binder may be prepared and analyzed by the following alternative exemplary method.

1. Assemble one or more aluminum (or steel) molds. Uniform 6.35 mm thick circular asphalt binder specimens are desirable for this exemplary method. Preferably, samples are prepared in triplicate.

2. Apply (lightly) high vacuum grease to the exterior surface of ring 12 to prevent bonding between ring 12 and specimen 18 and to reduce any friction between the asphalt binder and the ring surface during the de-molding process (i.e., removal of the specimen from the mold).

3. Place thin plastic film (e.g., transparency film for a laser printer) on top of base plate 22 to facilitate removal of specimen 18 following casting; position centering plate 20 and tighten dowel pin(s) 32; and attach specimen supports 26 and 28 with the shoulder bolts 30.

4. On the inside, arced surface of specimen supports 26 and 28, place a strip of plastic. Light application of vacuum grease to both ends of plastic strip facilitates the placement of the plastic strip on specimen supports.

5. Heat a quantity of asphalt binder to about 150° C. until the binder becomes sufficiently fluid-like. Pour the liquefied binder into the ring-shaped area in the mold between the specimen supports and the ring. Because the liquefied binder contracts as it cools, it may be necessary to slightly overfill the mold to create a specimen having the desired size characteristics.

6. Allow the specimen to cool to room temperature. Using a heated spatula trim off any excess asphalt binder from the mold. Place the de-molded specimens (in triplicate) in the microprocessor controlled environmental chamber and pretreat for 30 minutes at minus 10° C.

7. Connect the electrical strain gauge and the thermocouple first to the input module (i.e., signal amplifier) and then to processor 50.

8. Lower the temperature from minus 10 to minus 40° C. at a rate of 10° C. per hour.

9. Run a data acquisition program, assign proper gauge factor for each electric strain gauge, and set the desired data collection time interval. The gauge factor of 2.115 for the strain gauges used was input into the Megadac system in the exemplary method.

10. Measure and record (i) the temperature of the chamber and the specimens (using a thermocouple placed in a blank or dummy specimen) and (ii) the strain readings of the test specimens at a rate of one reading per second. Note: When a relatively slow cooling rate (e.g., 10° C./hour) is used, a single thermocouple is adequate for gathering data; however, if a more rapid cooling rate is used, extra thermocouples imbedded in extra asphalt specimens may be needed because at the more rapid cooling rate, the temperature inside of the asphalt binder will be significantly different from the temperature of the environmental chamber.

11. Determine the cracking temperature and calculate the thermal stress experienced by the test specimens.

12. Temperature calibration is done once before testing specimens. As the temperature drops, length of metal foil in the strain gauge and the aluminum ring change, resulting in varying strain readings of an empty ring at different temperatures. Temperature calibration is done by collecting test time, strain of the empty ring (without asphalt binder), and temperature as temperature is lowered as in the actual specimen testing. The difference of the strains of ring 12 with and without binder specimen is the strain attributed to the thermal load due to the differential contraction between the asphalt binder and the aluminum ring.

13. Data (time and strains) collected by Megadac were exported as text format and read into a Micrsoft Excel spread sheet. Time and temperature were collected manually and combined with the Megadac data in Excel for determination of the cracking temperature and the tensile strength of the specimen by plotting temperature versus strain. The data in Excel spread sheet program were in tabular form with time in second, temperature in centigrade Celsius (° C.), and strain in microstrain (µε).

Determination of Cracking Temperature

Figure 4:
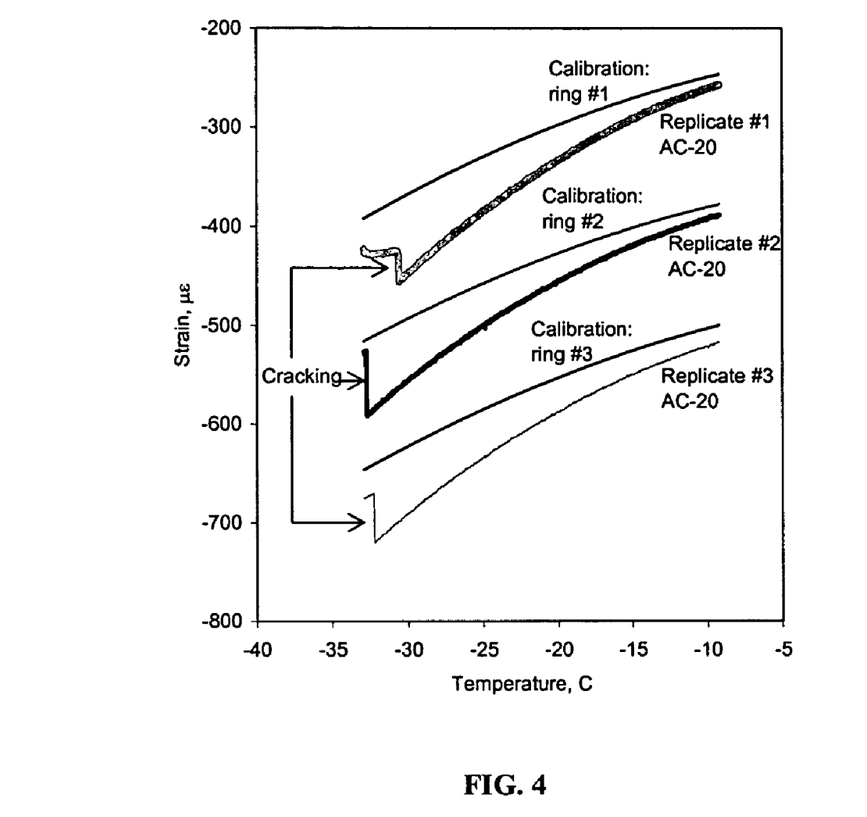
FIG. 4 is a data plot showing the uncorrected strain of the specimen (sample reading) and the baseline reading (temperature calibration with empty aluminum ring) versus temperature.

For determination of the cracking temperature, no calculation is necessary. A plot of uncorrected strain (or corrected for temperature by subtracting baseline strain determined from the ring temperature calibration) versus temperature is constructed. As the temperature drops, the contraction of the asphalt binder is considerably greater than that of the aluminum ring, and thus the ring experiences compressive strain. Because the stiffness (modulus) of the binder specimen rapidly increases as the temperature is lowered, stresses on the binder specimen and the ring also increases as the temperature is lowered. When the stress on the asphalt binder specimen reaches the tensile strength of the binder, the specimen cracks (fails) and the stress is relieved. This release of stress in the specimen is shown as the abrupt reduction of strain experienced by the ring. The cracking temperature directly correlates to this abrupt relief of the compressive strain. FIG. 4 is a graphic representation of this effect. In this experiment, strain readings of test specimens were taken every one second and were plotted together with the temperature calibration of three rings in FIG. 4. The cracking temperature of the specimens ranges from −30.6 to −32.7° C.

Calculation of Thermal Stress

Figure 5:
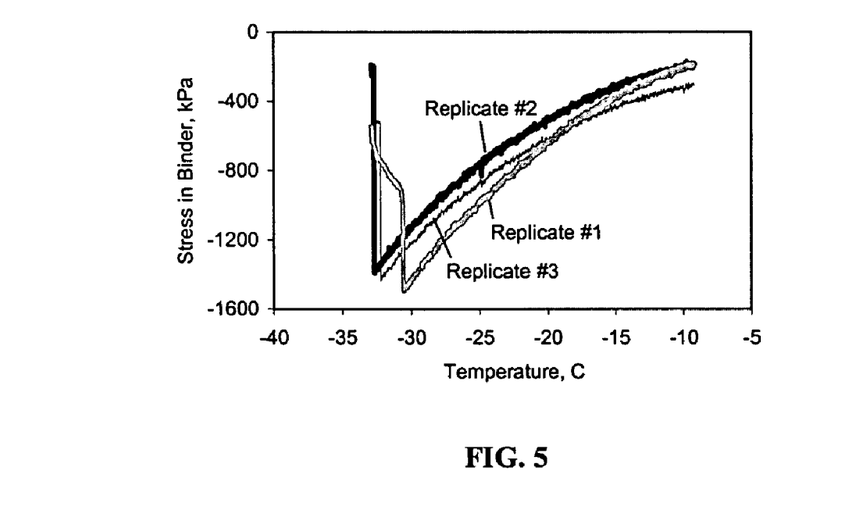
FIG. 5 is a data plot showing thermal stress development versus temperature during an experimental analysis of an asphalt binder specimen.

For the calculation of thermal stress, a temperature correction is required. As with all other materials, strain gauges also contract and expand as the temperature changes, thereby affecting the strain readings at different temperatures. A baseline temperature scan is performed for each ring 12, i.e., testing empty aluminum ring. Then, the corrected strain, the force in the aluminum ring, and the thermal stress in the binder specimen can be determined as:

$$\epsilon_{corr} = \epsilon_{test} - \epsilon_{calib}$$

$$F_{ABCD} = \epsilon_{corr} \cdot E_{ABCD} \cdot A_{ABCD}$$

$$\sigma_b = F_{ABCD}/A_b$$

where, $\epsilon_{corr}$=strain gauge reading corrected for temperature
$\epsilon_{test}$=strain gauge reading of the aluminum ring tested with the asphalt binder
$\epsilon_{calib}$=strain gauge reading of the aluminum ring tested without an asphalt binder
$F_{ABCD}$=thermal force in the aluminum ring
$E_{ABCD}$=modulus of elasticity of the aluminum ring
$A_{ABCD}$=cross-sectional area of the aluminum ring
$A_b$=cross-sectional area of the asphalt binder
$\sigma_b$=thermal stress in the asphalt binder FIG. 5 shows thermal stress developing in the three test specimens during the experiment. The tensile strength of the specimen at the cracking temperature ranges from 1390 kPa to 1500 kPa. Note: Young's modulus (modulus of elasticity) of aluminum ($10.0 \times 10^3$ ksi,), was used for the calculating the thermal stress in this example.

In summary, asphalt binders have much larger coefficients of thermal expansion and contraction than aluminum and when asphalt binders are subjected to falling temperatures, the differential thermal contraction (i.e., the more rapid contraction of asphalt binder than that of aluminum) creates thermal stress and eventually thermal cracks in the asphalt binder. When an asphalt specimen is placed around ring 12, the contraction of the specimen caused by a decrease in external temperature creates strain in the aluminum of the ring. This strain is measured by the electrical strain gauge 14, and may be used to calculate the stress experienced by the asphalt binder specimen. When the asphalt specimen reaches the limit of its tensile strength, the specimen will crack, and the release of the thermal stress in the specimen can be detected as a sudden decrease in the measurable strain experienced by ring 12. Thus, the cracking or failing temperature of the asphalt binder is directly determinable as the temperature at which the sudden drop of measured strain occurs. The device of the present invention can induce a thermal crack within a binder specimen in a manner similar to what occurs to pavement in the field. The device can be used to measure the cracking temperature and the thermal stress.

Compared with the existing methods to determine the critical temperature for thermal cracking of an asphalt binder, the present invention offers the following advantages: (i) easy determination of the thermal cracking potential of asphalt binders without elaborate assumptions and calculations; (ii) the test method of this invention may accommodate various field environmental conditions and mixture properties by adjusting the cooling rate and specimen/test geometry; (iii) determination of thermal stress and strength with simple calculations; (iv) fast measurement: because a single temperature scan is required in testing multiple specimens for the cracking temperature determination, the exemplary method takes less time than others methods which require multiple single-specimen tests at different temperatures; (v) simultaneous testing of many specimens: theoretically, up to 60-90 specimens can be placed and tested together in the 0.036 m³ environmental chamber used in this study; (vi) minimal source of errors: because no mechanical loading device is needed for this system, errors associated with a mechanical loading do not exist; (vii) specimen-blind test: because the field thermal cracking phenomena are simulated reasonably well with the test parameters, test results are believed to be representative of the field thermal cracking behavior and believed to be independent of specimen type, e.g., modified or unmodified; and (viii) simple procedure: overall, there is minimal operator interference during the test, making the procedure simple and straight-forward.

The following exemplary embodiment of the present invention provides an alternate system and method for determining the cracking temperatures of asphalt binder materials or other materials. The asphalt binder tested with this embodiment is typically an asphalt-based cement that is produced from petroleum residue either with or without the addition of particulate organic modifiers of size less than 250 gm. This system can be used with un-aged or aged binder material and is designed for testing within the temperature range from about +20 to −60° C. In the context of this invention, a fracture strain is defined as the amount of strain that the asphalt binder specimen releases when it cracks. For the purpose of lowering cracking temperatures to the range of values commonly observed at field, in this embodiment, certain modifications were made to the molds, ring material and specimen geometry.

The system of this embodiment uses a simple and efficient procedure for obtaining the critical temperatures of asphalt binders from thermal cracking. Initially, asphalt binder samples are heated and poured outside of an invar (or other material) ring placed in the center of a silicone mold. The invar ring includes a strain gauge to record the strain applied to it by contraction of the asphalt binder during cooling. Specimens are cooled at a constant rate and the cracking of the asphalt binder specimen is represented as a jump in strain on a real-time plot. Critical cracking temperature is determined by reading the temperature at the jump in strain on a strain vs. temperature plot. The fracture strain is recorded, and through calculations, the thermal stress of the asphalt binder specimen at the cracking temperature is determined.

This embodiment offers several distinct advantages, including that (i) the low-temperature thermal cracking can be determined directly without elaborate assumptions and complicated calculations; (ii) the cracking mechanism in this test is similar to field pavement because the asphalt specimen is restrained from contracting; (iii) faster measurements can be made since the test device requires a single temperature scan to determine the cracking temperature of multiple specimens; (iv) multiple specimens can be tested simultaneously; (v) the thermal stress and strength can be determined with simple calculations from data gathered from the test device; (vi) there are minimal sources of errors. Because no mechanical loading device is involved in this analysis, errors associated with mechanical loading are typically not present. Also, because specimens are poured directly and tested on the device, errors caused by handling and aligning are minimized.

Figure 6:
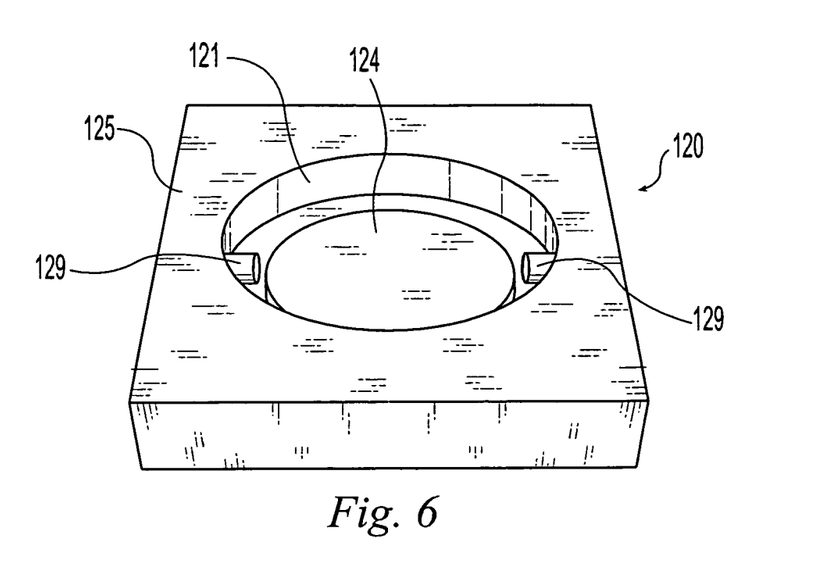
FIG. 6 is a front perspective view of the flexible embodiment of the mold.
Figure 7:
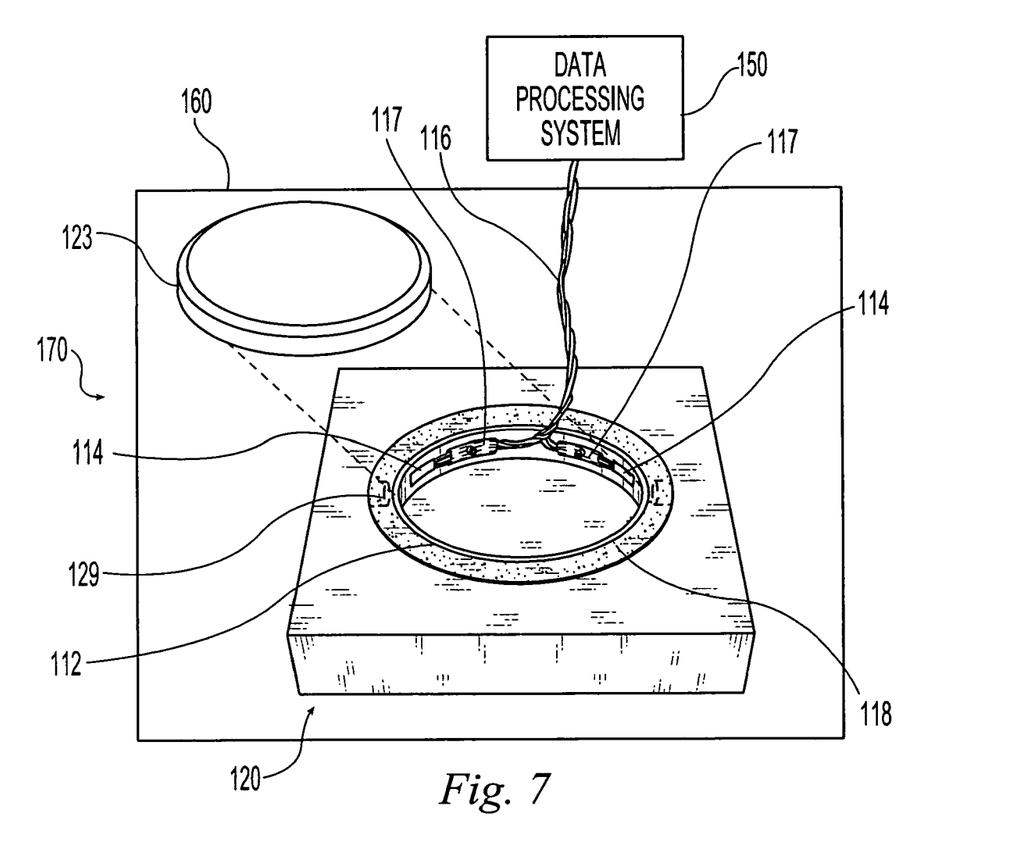
FIG. 7 is a front perspective view of the embodiment of the system of the present invention that includes the flexible mold.
Figure 8:
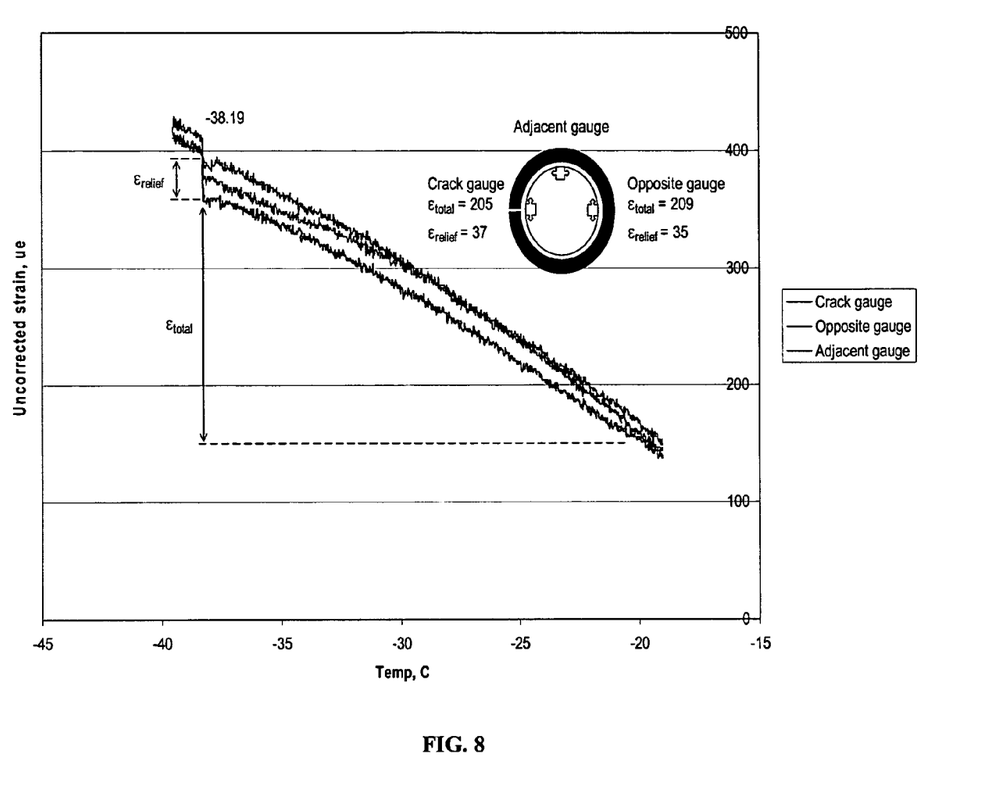
FIG. 8 is graph of cracking temperature and strain relief due to cracking.

With reference to FIGS. 6-8, the exemplary embodiment of system 170 includes a number of basic components. A vacuum oven is used to heat a test sample until it is sufficiently fluid to pour and to degas the samples to remove trapped air. A programmable environmental chamber 160 cools specimen 118 at a constant rate to temperatures of down to minus 60° C. Preferably, chamber 160 has a temperature range of −65 to 200° C. and two cubic feet of chamber space that can hold up to 100 specimens. Chamber 160 should also be equipped with an electronic programming device that has the capability of programming the cooling rate of the chamber. A computer-controlled data acquisition system 150 records real-time strain (from strain gauges), temperature (from thermocouples), and time readings at regular intervals. Using data acquisition software (such as LabVIEW), a real-time plot of the strain can be viewed as the sample is cooled. From this plot, a crack of specimen 118 can be seen as a jump in strain.

With reference to FIG. 4, single-piece mold 120 are used to prepare and hold the asphalt binder specimens 118 for testing. In the exemplary embodiment, a mold 120 is made by casting liquid silicone rubber into another mold to form a base 125, well 121, centering plate 124, and at least one 6.35 mm diameter cylindrical protrusion 129 at center height within well 121. Protrusion 129 creates a hole in the asphalt specimen to decrease its cross-sectional area and induce cracks at one or more specific locations. Molds having a shore hardness of 45 and 30, were used in Example II, below. Lower shore hardness corresponds to greater flexibility of the silicon. Use of a silicone mold reduces the handling of specimen 118, thus decreasing the chance that handling will affect test results. The silicone mold maintains flexibility at the lower temperatures so no excess strain is applied to the test specimen during testing. Mold 120 also does not prevent the asphalt specimens 118 from contracting. A release agent (see below) is used to prevent the asphalt binder from adhering and interacting with the silicone mold 120. A heated spatula may be used to trim excess asphalt binder flush with the top of mold 120 during the preparation step.

The exemplary test ring 112 has the dimensions 50.8 mm (outside diameter)×12.7 mm (height)×1.65 mm (thickness). This ring 112 is placed inside well 121, and asphalt binder is poured into the annular space formed between ring 112 and mold 120 (see FIG. 5) when ring 112 is properly centered on centering plate 124. The ring provides restraint as the asphalt binder contracts during the cooling process. This restraint is measured in strain, which is collected and recorded from a sensor 114, i.e., a strain gauge and/or a thermocouple attached to the inner surface of ring 112, by a data acquisition and processing system 150. One or more 350-Ohm electrical strain gauges may be attached to the inside of each test ring 112. In some embodiments, connecting wires 116, which are attached to sensor 114, are equipped with a snap-on connectors that allow electrical connections to be made without placing undesirable stress on the wiring. In some embodiments, wires 116 are secured to the inside of test ring 112 by a sleeve 117 that surrounds the wires and includes a small screw or similar means for attaching sleeve 117 to the inner surface of the ring 112.

Contraction of a metal 112 during cooling relieves thermal strain within specimen 118 and lowers cracking temperature. Other materials, such as aluminum, steel, and invar may be used for creating ring 112. Aluminum, steel, and invar have coefficients of thermal expansion (CTE) of $24 \times 10^{-6}$, $12 \times 10^{-6}$, and $1.4 \times 10^{-6}/°$ C. respectively. Aluminum and steel rings may be made from tubing with minimal surface preparation, while the invar rings are typically machined from a 2.25-inch solid rod. In the experiments described below, the invar rings produced the highest cracking temperature due to its very small coefficient of thermal expansion, which causes almost complete restraint during cooling. The aluminum and steel rings shrink along with the asphalt to provide strain relaxation and therefore, crack at lower temperatures.

A variety of materials and methods are typically used with this embodiment of the present invention for preparing and handling the test specimens 118. A release agent made with a 1:1 ratio of talc and glycerin is used on the inside of the silicone mold 120 and around the outside and bottom of the ring 112 to prevent adhesion and possible interaction with the asphalt binder. Acetone is used to clean the mold and ring after testing is completed and the specimen has been removed and analyzed. Cleaning cloths (preferably gauze) are used to clean molds 120 and rings 112 along with acetone after the test is completed. Asphalt binder is be poured in individual tin containers and stored until reheated and tested. Tin lids 123 (see FIG. 5) are used to cover the interior of ring 112 in order to protect the sensor 114 and wiring 116 inside while hot asphalt binder is being poured into mold 120. Aluminum foil is used to create a spout for the tin in order to have better control and accuracy when pouring the hot asphalt binder. The tin containing the asphalt binder sample is placed in a steel cup to slow heat dissipation when pouring several samples.

In preparation for an analytical run, a vacuum oven is set to the appropriate temperature for the sample that is being prepared and the oven is allowed to heat to the required temperature before placing the tin containing the asphalt binder specimen into the oven. Clean gauze and acetone are used to thoroughly clean silicone molds 120 and rings 112 before testing. Data processing system 150 is activated and the data analysis software is loaded. Preferably, all the equipment is calibrated to provide optimum performance for each test.

Having generally described this embodiment, a further understanding can be obtained by reference to the example detailed below, which is provided for purposes of illustration only and are not intended to be all inclusive or limiting unless otherwise specified.

EXAMPLE II

A test specimen 118 of asphalt binder may be prepared and analyzed by the following alternative exemplary method.

Preparation of Molds and Test Specimens

1. An aluminum foil spout is wrapped around the tins in order to provide better control and accuracy when pouring the hot asphalt binder. The tins are then placed in a steel cup to slow heat dissipation when pouring several samples.

2. The asphalt binder is heated in the tins for one hour in order to be sufficiently fluid to pour. The AASHTO binder specifications recommend minimum pouring temperature that produces a consistency equivalent to that of SAE 10W30 motor oil (readily pours but not overly fluid) at room temperature. After the initial heating, the asphalt binder samples are degassed in the vacuum oven at 0.09 MPa for 15 minutes to remove entrapped air.

3. The silicone molds 120 are prepared by applying a release agent of talc and glycerin (with a 1:1 mass ratio) to the specimen forming surfaces. The coating is applied as a uniform layer to prevent the asphalt binder from bonding with the mold. The outside and bottom of the rings are also coated with the release agent and then seated in the mold making sure the ring is level with the top. The sensor 114 (i.e., strain gauge) on ring 112 is positioned next to protrusion 129 in mold 120 to accurately measure the fracture strain. A tin lid 123 is placed over the inside of ring 112 to cover and protect the strain gauge and wiring inside while the hot asphalt binder is poured.

4. The steel cups containing the heated asphalt binder are then taken out of the oven and the binder is stirred to make sure the asphalt binder is thoroughly mixed.

5. The hot asphalt binder is poured into mold 120 starting at one spot, letting the binder reach the top and then moving around mold 120 in a single pass. The binder is poured in a continuous stream as quickly as possible to avoid a drop in temperature and from entraining air bubbles or gaps. By the protrusion 129, the asphalt binder is allowed to fill the bottom part of protrusion 129 before pouring across the top. The mold 120 is to be slightly overfilled because the binder shrinks upon cooling.

6. The asphalt binder test specimen 118, mold 120, and ring 112 are then allowed to cool at an ambient temperature (25° C. or lower) for thirty minutes.

7. Using a heated spatula, the excess asphalt binder is trimmed flush with the top of the mold and ring. It is important to keep the spatula heated and not to apply too much force on the binder when trimming a softer asphalt specimen, as it is prone to being pulled and stretched from its set shape.

8. The corners of the silicone molds 120 are bent back to make sure they are separated from the asphalt binder. Then ring 112 is carefully twisted to separate it from the test specimen 118 and release any bonding. Ring 112 is then twisted back to its original position so the sensor 114 (i.e., strain gauge) is lined up with protrusion 129. The rings will typically release easily if they are well coated with the release agent. If necessary, ring 112 is reseated in mold 120 by pressing tin lid 123 on ring 112.

9. A dummy sample is prepared to record the temperature change of the asphalt binder specimens as the test takes place. The dummy sample is made by placing a pre-made, pre-cracked, stiff asphalt binder ring between a silicone mold and an invar ring. Three thermocouples are placed in this sample; one between the ring and specimen; one between the sample and mold; and one embedded between a 0.25 inch thick piece of asphalt. These three thermocouples are connected to data processing system 150 to record the temperature in these three different locations as the test is run.

Test Procedure

1. The sensors 114, i.e., strain gauges, are hooked up to the data processing system 150 using the connectors on ring 112.

2. The data acquisition software (LabVIEW) is opened and the strain gauges are checked to make sure they are working properly.

3. The asphalt binder specimens and the dummy samples are placed in environmental chamber 160, which is set to a temperature of 20° C. A program is then started on environmental chamber 160 to cool the samples to −20° C. in one hour (40° C./hr). Once the temperature reaches −20° C., the next stage of the program starts, and the specimens are cooled at a rate of 10° C./hr.

4. At the beginning of the cooling process the data acquisition software (LabVIEW) program is launched to record strain and temperature readings at ten-second intervals.

5. A real-time plot of the strain is shown on the data acquisition software (Lab VIEW) program. The test is ended when the specimens crack, producing a sudden jump in strain.

6. The program on environmental chamber 160 is stopped and the chamber is turned off. The specimens are then taken out of the chamber.

7. The specimens 118 are inspected to see where each specimen cracked. Each asphalt binder specimen is then taken out of each mold 120 and inspected for defects such as cold joints or bubbles from trapped air.

8. The silicone mold 120 and invar ring 112 are then cleaned with acetone and safely stored until the next test.

9. Typically, at least three specimens of the same asphalt binder are tested during the same test run. Multiple specimens may help to identify any possible outliers. Also, if one specimen shows any unusual result, it can be compared with the other specimens tested to determine the cause.

Determining the Cracking Temperature and Failure Strain

1. The data file of the test is opened in Excel and a plot of strain versus temperature of the asphalt binder specimens 118 is created.

2. The critical cracking temperatures of the asphalt binder specimens are taken directly from the plot where there is a jump in strain.

3. The failure strain is read on the strain versus temperature graph created in step 1 (above, in this section). The failure strain is amount of strain that jumped when the specimen cracked.

Calculations for Finding Failure Stress from Failure Strain

1. For calculation of thermal stress, a strain correction is required. Strain gauges contract and expand as the temperature changes, which affect the strain readings. Therefore, a baseline temperature scan is preformed to calibrate each empty ring 112. Note: in the equations below, the test ring 112 is referred to as "ABCD ring."

2. The corrected strain for the asphalt specimens can be determined by subtracting the test strain readings from the calibration strain of the ring as shown in the following equation:

$$\epsilon_{corr} = \epsilon_{calib} - \epsilon_{test}$$

where:

$\epsilon_{corr}$=corrected strain gauge reading, $\mu\epsilon$ $\epsilon_{test}$=strain gauge reading of the ABCD ring tested with asphalt binder, $\mu\epsilon$ $\epsilon_{calib}$=strain gauge reading of the ABCD ring tested without asphalt binder, $\mu\epsilon$ 3. The thermal force is calculated by using equation the following equation:

$$F_{ABCD} = \epsilon_{corr} E_{ABCD} A_{ABCD}$$

where:

$F_{ABCD}$=thermal force in the ABCD ring, N $\epsilon_{corr}$=corrected strain gauge reading, $\mu\epsilon$ $E_{ABCD}$=modulus of elasticity of the ABCD ring, Pa $A_{ABCD}$=cross-sectional area of the ABCD ring, m$^2$ 4. Then, the thermal stress is calculated using the following equation:

$$\sigma_{AC} = F_{ABCD}/A_{AC}$$

where:

=thermal stress in the asphalt binder, PA $F_{ABCD}$=thermal force in the ABCD ring, N $A^{AC}$=cross-sectional area of the asphalt binder, m$^2$ Report of Specimen Analysis Following the procedure described above, a report is typically generated that includes: sample/specimen identification, the date and time of testing, the rate of cooling, the cracking temperature for each specimen to the nearest 0.1° C. as determined from the graph of strain vs. specimen temperature, the fracture strain to the nearest 0.1 microstrain, the fracture stress to the nearest 0.01 MPa, the location of the crack in reference to strain gauge, any defects in ring 112 observed upon inspection, and whether or not the asphalt binder specimen bonded to ring 112.

The combination of invar rings and the silicon molds having shore hardness of 45 provided the closest cracking temperature compared to the PG grading and the best standard deviation of approximately 1° C. The average strain relief is the amount of strain that a test specimen 118 releases when it cracks and the average strain total is the amount of strain the specimen develops from −20° C. until the cracking temperature. Rings 112 are typically positioned so that one strain gauge is next to one of the holes in the specimen. The strain total is taken from that gauge, and it can be seen from the results in FIG. 8 that the strain development next to both holes is relatively the same.

While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed:

1. A system for analyzing materials, comprising:
   (a) a test sample;
   (b) a mold for containing a test specimen, wherein the test specimen comprises the test sample and wherein the shape of the test specimen is determined by the mold;
   (c) a device for characterizing the test specimen, wherein the device further comprises:
   (i) a ring in communication with the test specimen;
   (ii) at least one sensor in communication with the ring; and
   (d) a means for changing the temperature of the test specimen at a controlled rate; and
   (e) a data processing system in communication with the sensor for processing data gathered from the sensor.

2. The system of claim 1, wherein the test sample further comprises asphalt binder.

3. The system of claim 1, wherein the mold further comprises:
   (a) a substantially circular casting area;
   (b) a plate within the casting area for centering the test specimen and ring within the casting area; and
   (c) at least one protrusion formed within the casting area for inducing a crack in the test specimen at a predetermined location.

4. The system of claim 1, wherein the mold is constructed from silicone, rubber, plastic, or metal.

5. The system of claim 1, wherein the ring is constructed from metal.

6. The system of claim 1, wherein the at least one sensor is a strain gauge.

7. The system of claim 1, wherein the at least one sensor is a thermocouple.

8. The system of claim 1, wherein the means for changing the temperature of the test specimen further includes an environmental chamber.

9. The system of claim 1, wherein the data processing system further comprises a computer, and wherein the computer further comprises data analysis software.

10. A method for analyzing materials, comprising:
    (a) heating a test sample;
    (b) placing a testing device within a mold, wherein the mold further comprises a well, and wherein the device is substantially centered within the well and defines an annular space therewith, and wherein the device further comprises:
        (i) a metal ring;
        (ii) at least one sensor in communication with the ring; and
    (c) creating a test specimen in the well by pouring the heated test sample into the annular space and allowing the test specimen to cool;
    (d) attaching the at least one sensor to a data processing system;
    (e) changing the temperature of the test specimen and the testing device at a controlled rate; and
    (f) processing the data received from the sensor as the temperatures of the test specimen and the testing device change over time.

11. The method of claim 10, further comprising:
    (a) lowering the temperature of the test specimen to about minus 60° C.; and
    (b) determining the cracking temperature of the test specimen from the data gathered by the data processing system.

12. The method of claim 10, wherein the test sample further comprises asphalt binder.

13. The method of claim 10, wherein the mold is constructed from silicon, rubber, plastic, or metal.

14. The method of claim 10, wherein the metal ring is constructed from aluminum, steel, or invar.

15. The method of claim 10, wherein the at least one sensor is a strain gauge.

16. The method of claim 10, wherein the at least one sensor is a thermocouple.

17. The method of claim 10, wherein changing the temperature of the test specimen and the testing device further includes the step of placing the specimen and the device in an environmental chamber.

18. The method of claim 10, wherein the data processing system further comprises a computer, and wherein the computer further comprises data analysis software.

* * * * *